United States Patent
Messadek

(10) Patent No.: US 7,780,990 B2
(45) Date of Patent: Aug. 24, 2010

(54) COMBINATION THERAPEUTIC COMPOSITIONS AND METHOD OF USE

(76) Inventor: Jallal Messadek, Place des Beguinages 2, B-4000, Liege (BE)

( * ) Notice: Subject to any disclaimer, the term of this patent is extended or adjusted under 35 U.S.C. 154(b) by 431 days.

(21) Appl. No.: 11/838,788

(22) Filed: Aug. 14, 2007

(65) Prior Publication Data

US 2008/0031964 A1 Feb. 7, 2008

Related U.S. Application Data

(63) Continuation-in-part of application No. PCT/BE2006/000040, filed on Apr. 27, 2006, and a continuation-in-part of application No. PCT/BE2005/000022, filed on Feb. 15, 2005.

(51) Int. Cl.
A61K 9/16 (2006.01)
A01N 37/30 (2006.01)

(52) U.S. Cl. ........................... 424/490; 514/556

(58) Field of Classification Search ................ None
See application file for complete search history.

(56) References Cited

U.S. PATENT DOCUMENTS

| | | | |
|---|---|---|---|
| 4,066,756 A | 1/1978 | Orr et al. | |
| 4,703,045 A | 10/1987 | Guinot | |
| 4,814,179 A | 3/1989 | Bolton | |
| 4,968,719 A | 11/1990 | Brevetti | |
| 5,716,941 A | 2/1998 | Rabinoff | |
| 5,876,780 A | 3/1999 | Vertanen | |
| 5,880,098 A | 3/1999 | Haussinger | |
| 5,928,195 A | 7/1999 | Malamud et al. | |
| 5,961,999 A | 10/1999 | Bimczok et al. | |
| 6,008,221 A | 12/1999 | Smith et al. | |
| 6,235,311 B1 | 5/2001 | Ullah et al. | |
| 6,287,765 B1 | 9/2001 | Cubicciotti | |
| 6,355,166 B1 | 3/2002 | Amarasinghe et al. | |
| 6,399,785 B1 | 6/2002 | Murphy et al. | |
| 6,476,006 B2 | 11/2002 | Flashner-Barak et al. | |
| 6,624,180 B2 | 9/2003 | South et al. | |
| 6,762,025 B2 | 7/2004 | Cubicciotti | |
| 6,855,734 B2 | 2/2005 | Messadek | |
| 6,881,420 B2 | 4/2005 | Flashner-Barak et al. | |
| 2002/0034757 A1 | 3/2002 | Cubicciotti | |
| 2002/0065320 A1 | 5/2002 | Messadek | |
| 2002/0183380 A1 | 12/2002 | Hunter | |
| 2003/0187074 A1* | 10/2003 | Hussain et al. | 514/635 |
| 2003/0203878 A1 | 10/2003 | Flashner-Barak et al. | |
| 2004/0033223 A1 | 2/2004 | Messadek | |
| 2004/0096499 A1* | 5/2004 | Vaya et al. | 424/468 |
| 2006/0034918 A1 | 2/2006 | Messadek | |
| 2006/0128657 A1 | 6/2006 | Messadek | |
| 2006/0160896 A1 | 7/2006 | Messadek | |
| 2006/0233877 A1 | 10/2006 | Messadek et al. | |
| 2007/0134324 A1 | 6/2007 | Messadek | |
| 2007/0213399 A1 | 9/2007 | Messadek | |

FOREIGN PATENT DOCUMENTS

| | | |
|---|---|---|
| BE | 1012546 | 12/2000 |
| BE | 1012712 | 2/2001 |
| BE | 2003/0248 | 4/2003 |
| DE | 19910682 | 9/2000 |
| EP | 0347864 | 12/1989 |
| EP | 0349902 | 1/1990 |
| EP | 0781554 | 7/1996 |
| FR | 2590 M | 3/1963 |
| FR | 70.47549 | 12/1970 |
| FR | 77 29075 | 9/1977 |
| HU | 210122 B | 9/1992 |
| JP | 2000-143486 | 5/2000 |
| JP | 10321984 | 5/2000 |
| WO | 9515750 | 6/1995 |
| WO | 9706795 | 2/1997 |
| WO | 9738685 | 10/1997 |

(Continued)

OTHER PUBLICATIONS

Savi et al., Abstract from Entrez-PubMed web page entitled "SR 121787, a new orally active fibrinogen receptor antagonist," Thromb Haemost, Sep. 1998;80(3):469-76., 1 page.

Banno et al., Abstract from Entrez-PubMed web page entitled "Antiaggregatory, antithrombotic effects of MS-180, a novel platelet glycoprotein IIb/IIIa receptor antagonist," Eur J Pharrnacol., Feb. 19, 1999;367(2-3):275-82., 1 page.

Ramjit et al., Abstract from Entrez-PubMed web page entitled "Antithrombotic effects of MK-0852, a platelet fibrinogent receptor antagonist, in canine models of thrombosis," J Pharmacol Exp Ther., Sep. 1993;266(3):1501-11, 2 pages.

(Continued)

Primary Examiner—Robert A Wax
Assistant Examiner—Jeffrey T Palenik
(74) Attorney, Agent, or Firm—Hovey Williams LLP

(57) ABSTRACT

The present invention provides pharmaceutical compositions and methods for the treatment of diabetes mellitus using combination therapy. The compositions relate to a compound selected from one or more of betaines, lipidic betaines, betaine lipids and an antidiabetic agent such as sulfonylureas, biguanides, glitazones, .alpha.-glucosidase inhibitors, potassium channel antagonists, aldose reductase inhibitors, glucagon antagonists, activators of RXR, insulin therapy or other anti-obesity agent. The methods include the administration of the combination of compound of Formula I with antidiabetic agent where the two components are delivered in a simultaneous manner, where the compound selected from one or more of betaines, lipidic betaines, betaine lipids is administered first, followed by the antidiabetic agent, as well as wherein the antidiabetic agent is delivered first followed by the compound selected from one or more of betaines, lipidic betaines, betaine lipids. In the claims, betaine means pharmaceutically acceptable betaine, lipidic betaines, betaine lipids, pharmaceutically acceptable salts thereof and combinations thereof.

39 Claims, No Drawings

FOREIGN PATENT DOCUMENTS

| WO | WO 97/38686 | 10/1997 |
|---|---|---|
| WO | 9819690 | 5/1998 |
| WO | WO 98/50497 | 12/1998 |
| WO | WO 99/45913 | 9/1999 |
| WO | 0025764 | 5/2000 |
| WO | 0051596 | 9/2000 |
| WO | WO 01/56609 | 8/2001 |
| WO | WO 02/00213 | 1/2002 |
| WO | WO 02/47493 | 6/2002 |
| WO | WO 02/062322 | 8/2002 |
| WO | WO 02/068002 | 8/2002 |
| WO | WO 2004/032916 | 4/2004 |
| WO | WO 2004/049095 | 6/2004 |
| WO | WO 2004/091601 | 10/2004 |
| WO | WO 2005/004854 | 1/2005 |
| WO | WO 2005/011642 | 2/2005 |
| WO | WO 2005/011645 | 2/2005 |
| WO | WO 2005/065675 | 7/2005 |
| WO | WO 2006/007671 | 1/2006 |
| WO | WO 2006/050581 | 5/2006 |
| WO | WO 2006/050585 | 5/2006 |

OTHER PUBLICATIONS

Hoffmann et al., Abstract from Entrez-PubMed web page entitled "Prevention of thrombosis and enhancement of thrombolysis in rabbits by SR 121787, a glycoprotein II/III antagnoist," J Pharmacol Exp Ther., Aug. 1998:286(2):670-5., 1 page.

Packham, Abstract from Entrez-PubMed web page entitled "Role of platelets in thrombosis and hemostasis." Can J Physiol Pharmacol., Mar. 1994;72(3):278-84., 1 page.

Lynch et al., Abstract from Entrez-PubMed web page entitled "Nonpeptide glycoprotein IIb/IIIa inhibitors. 5. Antithrombotic effects of MK-0383," J Pharmacol Exp Ther., Jan. 1995;272(1):20-32., 2 pages.

Katada et al., Abstract from Entrez-PubMed web page entitled "The in vitro and in vivo pharmacological profiles of a platelet glycoprotein IIb/IIIa antagonist, NSL-9403," Thromb Res., Oct. 1, 1997;88(1):27-70., 1 page.

Ogawa et al., Abstract from Entrez-PubMed web page entitled "Antiplatelet and antithrombotic effects of orbofiban, a new orally active GPIIb/IIIa antagonist, in guinea pigs," Thromb Res., Mar. 1, 2000;97(5):307-15., 1 page.

Zapadniuk, Abstract from Entrez-PubMed web page entitled "Cholagogic effect of trimethylglycine in normal animals of different ages and in experimental atherosclerosis," Biull Eksp Biol Med., Jul. 1987:104(7):30-2., 2 pages.

Panteleimonova, Abstract from Entrez-PubMed web page entitled "Effect of trimethylglicine on lipid metabolism in experimental atherosclerosis in rabbits," Farmakol Toksikol, Jul.-Aug. 1983;46(4):83-5., 1 page.

Fazio et al., "Treatment of Human Atherosclerosis with Betaine," Minerva Med. Apr. 25, 1961, pp. 1511-1516, XP-000853747.

P.H. List et al., "Hagers Handbuch Der Pharmazeutischen Praxis," 1972, Pringer Verlag, Berlin Heidelberg, New York, p. 431, XP-002123167.

Wilcken et al., "The natural history of vascular disease in homocystinuria and the effects of treatment," J. Inher. Metab. Dis. 20(1997) 295-230.

Betaine for Homocystinuria, The Medical Letter, vol. 39, Issue 993, Jan. 31, 1997, p. 12, XP-000853853.

Reynolds, Betaine Hydrochloride, Matindale, The Extra Pharmacopoeia, 1996, Royal Pharmaceutical Society, London, p. 1679, XP-002123168.

1225. Betaine, The Merck Index, 1996 Merck and Co., Whithouse Stations, NJ, p. 198, XP-002123169.

Mar et al., Abstract from Entrez-PubMed web page entitled "Betaine in wine: answer to the French paradox?" Med Hypotheses, Nov. 1999;53(5):383-5., 2 pages.

Salamone et al, "Changes in blood coagulation in experimental subacute poisoning with p-dichlorobenzene, The influence of some lipotropic factors," Journal, Answer 13 of 13, Copyright 2003, ACS, 1 page.

Vinson et al., "New Drug Approvals of 1996-Part 3," Drug Topics, Mar. 17, 1997, University of Mississippi School of Pharmacy, pp. 72-81.

Naproxen betainate Pharmaprojects, Applied Pharma Research, PJB Publications Ltd., Richmond, Surrey, UK, XP-002202249, pp. 1-2.

Matthews et al., An indirect response model of homocysteine suppression by betaine: optimising the dosage regimen of betaine in homocystinuria,: 2002 Blackwell Scient Ltd Br J Clin Pharmacol, 54, 140-146.

Schwahn et al, "Pharmacokinetics of oral betaine in healthy subjects and patients with homocystinuria," 2003 Blackwell Scient Ltd Br J Clin Pharmacol, 55, 6-13.

Naproxen monography from http://www.rxlist.com/, Clinical Pharmacology, pp. 1-2.

Bandfield et al., "Naproxen, Naproxen Sodium, and Naproxen Betainate Sodium Monohydrate Salts," Pharmaceutics 1, Apr. 14, 2001, pp. 1-5.

Van Hecken et al., Abstract from Entrez-PubMed web page entitled "Effect of clopidogrel on naproxen-induced gastrointestinal blood loss in healthy volunteers," Drug Metabol Drug Interact, 1998;14(3):193-205., 1 page.

EC-Naprosyn, Naprosyn, Anaprox, Naprosyn, Rx Only, Roche Pharmaceuticals, Copyright 1999-2004 by Roche Laboratories Inc., pp. 1-20.

Environmental and Health Assessment of Substances in Household Detergents and Cosmetic Detergent Products, Environment Project, 615, 2001, 6.1 Betaines, http:www2.mst.dk/common/Udgivramme/Frame.asp?pg=http://www2.mst.dk/udgiv/Publications/2001/87-7944-596-9/html/helepubl_eng.htm, 1 page.

NIAID Home/Anti-HIV/OI Chemical Compound Search/Anti-HIV/OI Chemical Compound Results, http:chemdb.niaid.nih.gov/struct_search/all/url_search.asp?aids_no=008188, 1 page.

Wyrick P.B. et al., The Microbicidal Agent C31G Inhibits Chlamydia Trachomatis Infectivity in vitro., Antimicrob Agents Chemother, Jun. 1997, 41(6): 1335-44, PMID: 9174195, 1 page.

Thompson, K.A. et al., Assessment of the Anti-Microbial Agent C31G as a Spermicide: Comparison with Nonoxynol-9, Contraception, May 1996, 53(5): 313-8, PMID: 8724622, 1 page.

Rogers J.S., Abstract from Entrez-PubMed web page entitled "Hypercoagulable states," W V Med J., Feb. 1993;89(2):61-3, 1 page.

Nielsen H.K., Abstract from Entrez-PubMed web page entitled "Pathophysiology of venous thromboembolism," Semin Thromb Hemost, 1991;17 Suppl 3:250-3, 1 page.

Silver et al., Abstract from Entrez-PubMed web page entitled "The caput medusae of hypercoagulability," J. Vasc. Surg., Feb. 2000;31(2):396-406, 1 page.

Swan M.A., "Improved Preservation of the Ram Spermatozoan Plasma Membrane using Betaine in the Primary Fixative," J. Microsc., Sep. 1997, 187(pt 3): 167-9, PMID: 9351233, 1 page.

Thomas, K.C. et al., Effects of Particulate Materials and Osmoprotectants on Very-High-Gravity Ethanolic Fermentaiont by Saccharomyces Cerevislae, Appl Environ Microbiol, May 1994, 60(5): 1519-24, PMID: 801734, 1 page.

Chambers, S. et al., The Osmoprotective Properties of Urine for Bacteria: The Protective Effect of Betaine and Human Urine Against Low pH and High Concentrations of Electrolytes, Sugars, and Urea, J. Infect Dis., Dec. 1985, 152(6): 1308-16, PMID: 3905988, 1 page.

Smith, L.T., Role of Osmolytes in Adaptation of Osmotically Stressed and Chill-Stressed Listeria Monocytogenes Grown in Liquid Media and on Processed Meat Surfaces; Appl Environ Microbiol, Sep. 1996, 62(9): 3088-93, PMID: 8795194, 1 page.

Peddie B.A. et al., Is the Ability of Urinary Tracy Pathogens to Accumulate Glycine Betaine a Factor in the Virulence of Pathogenic Strains?, J. Lab, Clin. Med., Oct. 1996, 128(4): 417-22, PMID: 8833891, 1 page.

Koskinen. E. et al., A Preliminary Study on the Use of Betaine as a Cryoprotective Agent in Deep Freezing of Stallion Semen, Zentralbl Veterinarmed A., Feb. 1989, 36(2): 110-4, PMID: 2501949, 1 page.

Swan M.A., Improved Preservation of Ultrastuctural Morphology in Human Spermatozoa Using Betaine in the Primary Fixative, Int. J. Androl., Feb. 20, 1997, (1): 45-54, PMID: 9202990, 1 page.

Office Action in U.S. Appl. No. 11/251,737 dated Apr. 17, 2008, 7 pages.

Office Action in U.S. Appl. No. 11/333,514 dated Sep. 20, 2007, 12 pages.

Office Action in U.S. Appl. No. 11/333,514 dated Nov. 15, 2007, 11 pages.

McGregor et al, "A Controlled Trial of the Effect of Folate Supplements on Homocysteine, Lipids and Hemorheology in End-State Renal Disease," Nephron, vol. 85, No. 3, 2000, 215-220.

Gurfinkel et al., "Fast platelet suppression by lysine acetylsalicylate in chronic stable coronary patients. Potential clinical impact over regular aspirin for coronary syndromes," Clin. Cardiol., Sep. 2000;23(9):697-700.

Klasing et al., "Dietary Betaine Increases Intraepithelial Lymphocytes in the Duodenum of Coccidia-Infected Chicks and Increases Functional Properties of Phagocytes," 2002, The American Society for Nutritional Sciences, J. Nutr, 132:2274-2282, 2002.

Schmidt et al., "Total nitric oxide production is low in patients with chronic renal disease," Kidney International, 2000, 58, 1261-1266.

Letter Regarding Dietary Supplement Health Claim for Folic Acid, Vitamin B6, and Vitamin B12 and Vascular Disease, to Jonathan W. Emord of Emord & Associates, PC, from Christine J. Lewis of the FDA, Nov. 28, 2000.

Malinow, "Plasma homocyst(e)ine and arterial occlusive diseases: a mini-review," Clin. Chem, Jan. 1995;41(1):173-6.

al Awami et al., "Homocysteine levels in patients with Raynaud's phenomenon," Vasa. May 2002; 31(2): 87-90.

Stammler et al., "The prevalence of hyperhomocysteinemia in thromboangitis obliterans. Does homocysteine play a role pathogenetically?" Dtsch Med Wochenschr, Nov. 15, 1996;121(46):1417-23.

English Translation of French Patent 2,590M issued on Jun. 15, 1964, 11 pages.

McCarty, "Co-administration of equimolar doses of betaine may alleviate the hepatotoxic risk associated with niacin therapy," Med-Hypothesis, Sep. 2000; 55(3): 189-94.

Letter regarding Petition for Health Claim: Folic Acid, Vitamin B6, and Vitamin B12 Dietary Supplements and Vascular Disease, to Jonathan W. Emord of Emord & Associatees from Christine J. Lewis of the FDA, Feb. 9, 2001.

Birnie et al., "Antimicrobial Evaluation of N-Alkyl Betaines and N-Alkly-N,N-Dimethylamine Oxides with Variations in Chain Length," Antimicrobial Agents and Chemotherapy, Sep. 2000, p. 2514-2517.

Palatka Karoly et al., "Changes in the expression and distribution of the inducible and endothelial nitric oxide synthase in mucosal biopsy specimens of inflammatory bowel disease," Scandinavian Journal of Gastroenerology, 2005, vol. 40, No. 6, pp. 670-680.

van Hoek, "Non-alcoholic fatty liver disease: a brief review," Scandinavian Journal of Gastroenerology Supplement, 2004;(241):56-9.

Mendes et al., "Recent advances in the treatment of non-alcoholic fatty liver disease," Expert Opin. Investig. Drugs, Jan. 2005;14(1):29-35.

Hiatt et al, Long-term safety of cilostazol in patients with peripheral artery disease: The CASTLE study (Cilostazol: A Study in Long-term Effects), Journal of Vascular Surgery, vol. 47, No. 2, pp. 330-336, Feb. 2008.

Korzh, "Relationship Between Endothelial Nitric Oxide Synthesis and Low-Grade Chronic Inflammation," European Atherosclerosis Society, 73rd EAS Congress, Salzburg, Austria, Jul. 7-10, 2002.

Didier et al., "Distal cutaneous necrosis, an unusual etiology: hyperhomocysteinemia," Ann Dermatol Venereol, Nov. 1999;126(11):822-5; PMID: 10612875.

Gurfinkel et al., "Fast Platelet Suppression by Lycine Acetylsalicylate in Chronic Stable Coronary Patients. Potential Clinical Impact Over Regular Aspirin for Coronary Syndromes," Abstracts—Myocardiol Ischemia and Infarction, JACC, Feb. 2000, 408A-409A.

Bonaa et al., Homocysteine lowering and cardiovascular events after acute myocardial infarction,: N. Eng. J. Med., Apr. 13, 2006; 354(15):1578-88. Epub Mar. 12, 2006.

Lonn et al., "Homocysteine lowering folic acid and B vitamins in vascular disease," N. Eng. J. Med., Apr. 13, 2006;354(15):1567-77. Epub Mar. 12, 2006.

Approval of Cilostazol, Jan. 6, 2006, Center for Drug Evaluation and Research, www.fda.gov/cder/news/cilostazol/appproval.htm.

Tafreshi, Medical Management of Peripheral Arterial Disease, Pharmacy Times, Bristol-Myers Squibb Company grant, 11 pages.

Diagnosis and Management of Peripheral Arterial Disease: A National Clinical Guideline, Scottish Intercollegiate Guidelines Network, Oct. 2006, www.sign.ac.uk.

Hiatt, "Medical Treatment of Peripheral Arterial Disease and Claudication," N Engl J Med, vol. 344, No. 21, May 24, 2001, pp. 1608-1621.

Hiatt, "The US experience with cilostazol in treating intermitten claudication," Atherosclerosis Supplements 6 (2006) 21-31.

Carman and Fernandez, "A Primary Care Approach to the Patient with Claudication," American Family Physician, vol. 61, No. 4, Feb. 15, 2000, http://www.aafp.org/afp/20000215/1027.htrnl, 8 pages.

Beaufour and Beaufour, "Nouvelles associations antinévralgiques à tolérance améliorée," Brevet Spécial De Médicament, P.V. No. 927. 734, No. 2.590, 1964, pp. 1-5.

Feb. 23, 1996 Chinese document (pp. 91-93) with English translation titled "Homocysteine and Vascular Disease," 5 pages.

Da Silva and Sobel. Abstract from Entrez-PubMed web page entitled "Anicoagulants: to bleed or not to bleed, that is the question," Semin Vasc. Surg. Dec. 2002:15(4):256-67, 1 page.

JACC Abstracts, Myocardial Ischemia and Infarction, Feb. 2000, 1196-107, pp. 408-409.

Lasch H.G., Abstract from Entrez-PubMed web page entitled "Principles of Drug Prevention of Thrombosis," Langenbecks Arch Chir., 1986;369:451-7, 1 page.

Marcel et al., Abstract from Entrez-PubMed web page entitled "From Virchow to red cells (the unended quest).", Ric Clin Lab., 1983;13 Suppl 3:71-81, 1 page.

I. Zöllei et al., Betaine-Palmitate Reduces Acetylsalicyclic Acid-induced Gastric Damage in Rats, Scand J. Gastroenterol 2001 (8), pp. 811-816.

Antithrombotic effect of Betaine, Bio Ethic, Jan. 2003, pp. 1-30.

Office Action in U.S. Appl. No. 09/945,391 dated Nov. 5, 2002, 5 pages.

Office Action in U.S. Appl. No. 09/945,391 dated Jun. 4, 2003, 14 pages.

Office Action in U.S. Appl. No. 10/635,048 dated Dec. 6, 2005, 8 pages.

Office Action in U.S. Appl. No. 10/635,048 dated Dec. 21, 2006, 16 pages.

Office Action in U.S. Appl. No. 10/635,048 dated Sep. 20, 2007, 25 pages.

Bidulescu et al., Usual choline and betaine dietary intake and incident coronary heart disease: the Atherosclerosis Risk in Communities (ARIC) Study,BMC Cardiovasc Disord. 2007, 7:20.

Hallas et al., "Use of single and combined antithrombotic therapy and risk of serious upper gastrointestinal bleeding: population based case-control study," BMJ 2006;333:726, Oct. 7, 2006.

Cassar, "Intermittent Claudication," BMJ, vol. 333, Nov. 11, 2006, pp. 1002-1005.

Apgar, "Efficacy of Cilostazol for Intermittent Claudication," American Family Physician, Feb. 15, 2000, 2 pages.

Girolami et al., "Treatment of Intermittent Claudication with Physical Training, Smoking Cessation, Pentoxifylline, or Nafronly," Arch Intern med, 1999;159:337-345.

Office Action in U.S. Appl. No. 11/747,167 dated May 12, 2008, 5 pages.

Giaid et al, "Expression of Endothelin-1 in the Lungs of Patients with Pulmonary Hypertension," NEJM, vol. 328:1732-1739, No. 24, Jun. 17, 1993, 2 pages.

Giaid et al. , "Reduced Expression of Endothelial Nitric Oxide Synthase in the Lungs of Patients with Pulmonary Hypertension," NEJM, vol. 333:214-221, No. 4, Jul. 27, 1995, 2 pages.

* cited by examiner

COMBINATION THERAPEUTIC COMPOSITIONS AND METHOD OF USE

This application is a continuation-in-part application of: 1) PCT/BE2006/000040 filed on Apr. 27, 2006, published under WO2006/113978; and 2) PCT/BE2005/000022 filed on Feb. 15, 2005, published under WO2006/086856 both of which are incorporated by reference herein.

FIELD OF INVENTION

In general, the present invention relates to pharmaceutical compositions, and more particularly, to pharmaceutical compositions for the treatment of diabetes mellitus using combination therapy.

BACKGROUND OF THE INVENTION

Diabetes mellitus is a term generally used to refer to various pathological states characterized by hyperglycemia and altered metabolism of lipids, carbohydrates and proteins. These conditions are also often associated with other co-morbidities, such as obesity and an increased risk of cardiovascular disease. By some estimates, as many as 600,000 new individuals become clinically diabetic every year in the United States.

Diabetic conditions are generally classified as either insulin-dependent diabetes mellitus (IDDM, Type I diabetes) or non-insulin-dependent diabetes mellitus (NIDDM, Type II diabetes). There are also less common clinical pathologies that are associated with diabetic conditions, such as gestational maturity-onset diabetes of youth (MODY), tropical diabetes secondary to chronic pancreatis, diabetes secondary to pancreatic disease or surgery, and diabetes secondary to endocrinopathies.

Virtually all forms of diabetes are due to a decrease in the circulating concentration of insulin (insulin deficiency) and/or a decrease in the response of peripheral tissues to insulin (insulin resistance). These abnormalities lead to alterations in the metabolism of carbohydrates, lipids, ketones and amino acids, and a hyperglycemic condition. IDDM appears to have an autoimmune etiology, which results in destruction of .beta. islet cells in the pancreas and the resulting inability to produce insulin. The etiology of NIDDM, the most prevalent form of diabetes, is more complex and possibly heterogeneous. Some loss of .beta.-cell volume is generally noted in these patients, as well as decreased circulating levels of insulin. NIDDM patients may also suffer commonly from insulin resistance.

The best-established therapy for all IDDM and many NIDDM patients is subcutaneous insulin treatment. Additionally, insulin is used as the treatment of choice for patients with post-pancreatectomy diabetes or gestational diabetes. While insulin is a key element in the control of these hyperglycemic conditions, there are a number of limitations associated with its use, including hypoglycemia, allergic reactions to insulin, lipoatrophy, lipohypertrophy, body weight gain, edema, and insulin resistance. There are a number of new forms of insulin on the market or in various stages of clinical evaluation, including new delivery systems, various recombinant forms, new routes of administration, and gene therapy. These novel forms of insulin treatments are believed to share some of the same limitations outlined above. A significant improvement in the treatment of diabetes can be achieved if insulin treatment is combined with agents that increase the insulin sensitivity of the peripheral tissues.

The concept of combination therapy is well exploited in current medical practice. Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). In real medical practice, it is often quite difficult to determine if drug combinations are additive or synergistic.

For most diabetic patients, treatment involves some form of insulin therapy. In addition, IDDM patients may receive a biguanide (e.g., metformin) to enhance the insulin utilization by peripheral tissues. NIDDM patients are often treated with a combination of insulin, a sulfonylurea (to enhance insulin production in the pancreas) and a biguanide or glitazone (to enhance insulin sensitivity by peripheral tissues). For example, the improved utility of a glitazone in combination with a sulfonylurea was recently demonstrated in human clinical trials (see, WO 98/36755). Recently, two glitazone compounds (rosiglitazone and pioglitazone) were approved in the United States for the treatment of NIDDM patients in combination with metformin.

A variety of antidiabetic compounds are known. For example, sulfonylureas are a group of drugs that induce hypoglycemia by stimulating insulin release from the pancreas. Generally, sulfonylureas have found wide utility in the treatment of NIDDM. Their efficacy is decreased in IDDM because of the inherent inability of the patient to produce insulin. Adverse reactions to sulfonylureas occur in a fraction of patients, particularly the elderly. One of the most severe side effects is hypoglycemia and coma. Other side effects include nausea and vomiting, cholestatic jaundice, agranulocytosis, cardiovascular mortality, aplastic and hemolytic anemias, generalized hypersensitivity reactions and dermatological reactions.

Biguanides are another group of drugs, first introduced in the mid 1950's, that have shown efficacy in the treatment of hyperglycemia by mechanisms that are not well understood. The best known agents of this type include metformin, phenformin and buformin. Unlike the sulfonylureas, metformin does not induce release of insulin from the pancreas. It is thought that its effects are mediated by increasing insulin activity in peripheral tissues, reducing hepatic glucose output due to inhibition of gluconeogenesis and reducing the absorption of glucose from the intestine. Side effects associated with the use of biguanides include lactic acidosis, diarrhea, nausea, and anorexia. These agents are often given in combination with drugs that increase the output of insulin from the pancreas, such as the sulfonylureas, which sometimes results in greater efficacy and/or the ability to use lower doses of the drugs, with an improved side effect profile.

More recently, the glitazones have been introduced and are widely used in the treatment of NIDDM. These agents, also known generically as thiazolidinediones, such as troglitazone, rosiglitazone and pioglitazone, are thought to work by increasing the sensitivity of peripheral tissues, such as skeletal muscle, towards insulin. They are often used in combination with insulin or other agents, such as the sulfonylureas, that enhance the release of insulin from the pancreas. A number of side effects have been described during the clinical evaluation of these agents, including hepatotoxicity, organomegaly, edema, anemia and body weight gain. While hepatotoxicity may be the most acutely life-threatening of these conditions, it does not appear in a large percentage of the patient population. On the other hand, the increases in body weight gain associated with chronic glitazone treatment are generally perceived as worsening an already critical co-morbid condition in the majority of the diabetic patients, and may ultimately result in the loss of antidiabetic efficacy for this type of agent after chronic treatment.

Alpha.-Glucosidase inhibitors, such as acarbose, reduce intestinal absorption of starch, dextrin, and disaccharides by inhibiting the action of intestinal brush border .alpha.-glucosidase. Inhibition of this enzyme slows the absorption of carbohydrates and the rise in plasma glucose that normally follows after a meal is blunted. Acarbose has shown some benefit in IDDM and NIDDM patients, but is often associated with dose-related malabsorption, flatulence and abdominal bloating.

Other types of agents that have found limited utility in treating diabetes include potassium channel antagonists such as repaglinide, and aldose reductase inhibitors such as zopolrestat and tolrestat. Still in the experimental stage, glucagon antagonists, activators of the retinoid-X receptor (RXR), activators of PPAR.alpha., activators of PPAR.delta. and anti-obesity agents are also being evaluated as potential antidiabetic agents.

In view of the foregoing, there remains a need in the art to provide more efficacious treatment for diabetic conditions and diabetic complications. Combination therapy treatments are needed that will reduce the amount of drugs taken, thereby decreasing side effects. Surprisingly it was found that combining the betaines, i.e. one or more compounds selected from one or more of betaines, lipidic betaines, betaine lipids, of the invention with antidiabetic agents enhance their effectiveness while lessening their potential side effects. The concomitant uses of betaines with antidiabetic agents permit to lower the amounts of the latter. The present invention fulfills these and other needs.

SUMMARY OF THE INVENTION

The present invention provides pharmaceutical compositions for the treatment of a variety of diseases, including diabetes mellitus, such as IDDM, NIDDM, gestational diabetes, juvenile diabetes, and the like, using combination therapy. In certain aspects, the pharmaceutical compositions comprise a pharmaceutically acceptable carrier with a compound of Formula I and an antidiabetic agent. Advantageously, the compositions of the present invention provide clinical advantage over the use of a single agent alone. As such, the present advantageous invention provides a combination or association or composition comprising: (i) a compound of Formula I: $(CH_3)_3N^+—(CH_2)n-COO^-$) n being an integer from 1 to 5 (preferably n=1) including pharmaceutically acceptable salts of compounds of Formula I, esters thereof, precursors thereof, and mixtures thereof; and (ii) one or more antidiabetic agents, including, but not limited to, sulfonylureas, biguanides, glitazones and other PPAR-.gamma agonists, PPAR.alpha. agonists, PPAR.delta. agonists, .alpha.-glucosidase inhibitors, potassium channel antagonists, aldose reductase inhibitors, glucagon antagonists, activators of RXR, insulin therapy or other anti-obesity agent (5), prodrugs thereof, or pharmaceutically acceptable salts of the antidiabetic agents, and a pharmaceutically acceptable carrier or diluent.

In certain aspects, the compositions of the present invention comprise a compound of Formula I formulated together with one or more antidiabetic agents. Alternatively, the compositions of the present invention comprise a compound of Formula I independently formulated with one or more antidiabetic agents i.e., separately formulated.

Suitable antidiabetic agents include, but are not limited to, sulfonylureas, biguanides, glitazones and other PPAR-.gamma. agonists, .alpha.-glucosidase inhibitors, potassium channel antagonists, aldose reductase inhibitors, glucagon antagonists, activators of RXR, activators of PPAR.alpha., activators of PPAR.delta., insulin therapy or other anti-obesity agents. The administration of a composition or combination comprising: (i) one or more compound of Formula I, which increase insulin production and/or increase peripheral tissue sensitivity to insulin, with (ii) an antidiabetic agent such as insulin therapy, or a stimulator of insulin secretion, and the like, increases the efficacy of either agent alone. In addition to increased efficacy, the combination therapy of the present invention allows for a concomitant reduction in the dose of the agents. The combination therapy of a compound of Formula I and one or more of another antidiabetic agents (e.g., biguanides, glitazones, RXR ligands, PPAR.gamma. agonists, etc.) results in a reduction in the side effects normally associated with certain antidiabetic agents.

In certain aspects, compounds of Formula I are administered successively (for example prior to the administration of the antidiabetic agent) or substantially simultaneously in combination with antidiabetic agents that are ineffective for stimulation of insulin secretion or insulin sensitivity, such as a-glucosidase inhibitors, potassium channel antagonists, aldose reductase inhibitors, glucagon antagonists, RXR ligands, PPAR.alpha. agonists, PPAR.delta. agonists, and anti-obesity agents. Surprisingly, these types of combination therapy result in enhanced efficacy relative to the use of the single agents alone.

In another embodiment, the present invention provides methods of treating metabolic or inflammatory disorders in a host by administering a composition of the present invention. In certain preferred aspects, the method includes the administration of a composition comprising a combination of a compound of Formula I with the antidiabetic agent delivered in a simultaneous manner, such as in a single formulation. In certain other aspects, the methods of the present invention include combination therapy wherein the compound of Formula I is administered at least partly first for example by means of a first formulation, followed by the antidiabetic agent administration for example by means of another or separate formulation. The methods also include an antidiabetic agent being delivered first in one formulation, followed by a compound of Formula I in a separate formulation. The present invention includes all such methods of administration. The combination therapy is especially efficacious on conditions associated with diabetes, such as obesity, cardiovascular diseases, cerebrovascular diseases, thrombosis, ischemia, hypoxia, hypertension, hypercholesterolemia, lipid disorders, peripheral neuropathies, Intermittent Claudication, metabolic syndrome . . . and other neurological disorders, and the like. The compound of formula I and the antidiabetic agent can be administered simultaneously, but preferably with a controlled release at least partly for the amount to be administered for the compound of formula I and/or for the amount of antidiabetic agent.

DEFINITIONS

Betaine or betaines as used in the claims means Betaines" such as compound of formula I, "lipidic betaines" and "betaine lipids", as well as combinations thereof.

The term "Betaines" as employed herein refers advantageously to compounds of formula I: $(CH_3)_3N^+(CH_2)_nCOO^-$ with n an integer from 1 to 5, (preferably glycine betaine n=1), pharmaceutically acceptable salts thereof, esters thereof, precursors thereof, and mixtures thereof.

The terms "lipidic betaines" and "betaine lipids" refer to betaine lipids which are structural components of membranes commonly found in ferns, mosses, fungi, amoeba, eukaryotes such as nonseed plants and algae. Betaine lipids are ether-linked, nonphosphorous glycerolipids that resemble the more commonly known phosphatidylcholine in overall structure. Most common glycerolipids are containing a diacyl-glycerol moiety to which a polar head group is attached. This head group can be a carbohydrate moiety as in the very abundant plant galactolipids or a phosphorylester as in the glycerophospholipids, the most common lipid class in animals. Betaine lipids represent a third class of glycerolipids in which a quaternary amine alcohol is bound in an ether linkage to the diacylglycerol moiety. They can be obtained by extraction, by biosynthesis or by synthesis. The betaine lipid diacylglyceryl-O-4'-(N,N,N-trimethyl)homoserine and a closely related isoform diacylglyceryl-O-2'-(hydroxymethyl)(N,N,N-trimethyl)-β-alanine are the most common.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to, those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form. Prodrugs of the compounds described herein are those compounds that readily undergo chemical changes under physiological conditions to provide the compounds of the present invention. Additionally, prodrugs can be converted to the compounds of the present invention by in vivo, chemical or biochemical methods in an ex vivo environment. For example, prodrugs can be slowly converted to the compounds of the present invention when placed in a reservoir such as transdermal patch and/or enteral reservoir and/or an implantable reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention can also contain unnatural proportions of atomic isotopes, stable isotopes etc., at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "prodrug" refers to compounds that are drug precursors, which, following administration, release the drug in vivo via a chemical or physiological process (e.g., a prodrug on being brought to the physiological pH is converted to the desired drug form).

"A combination amount sufficient," "an effective combination amount" "therapeutically effective combination amount" or "an effective amount of the combination of" all refer to a combined amount of both a compound of Formula I and the antidiabetic agent that is effective to ameliorate symptoms associated with diabetic diseases. As used herein, the term "combination" of compound of Formula I with an antidiabetic agent means the two compounds can be delivered in a simultaneous manner, in combination therapy wherein the compound of Formula I is administered first, followed by the antidiabetic agent, as well as wherein the antidiabetic agent is delivered first, followed by a compound of Formula I. The desired result can be either a subjective relief of a symptom(s) or an objectively identifiable improvement in the recipient of the dosage.

The terms "synergistic effective amount" refers to a combined amount of both a compound of Formula I and an antidiabetic agent that is effective to cause a synergistic effect. Synergy is a biological phenomenon in which the effectiveness of two active components in a mixture is more than additive, i.e., the effectiveness is greater than the equivalent concentration of either component alone. In certain aspects, the effectiveness of the combination therapy of a compound of Formula I and an antidiabetic agent is synergistic. Thus, synergism is a result, or function, that is more than the sum of the results, or functions of individual elements.

The term "simultaneous manner" and "combination treatment" refer to an administration protocol wherein the compounds of the present invention and at least one antidiabetic agent are administered within a single 24-hour period.

In one embodiment the period can be longer such as a week, a month, 3 months, 6 months, etc. Such longer periods are necessary when the compounds of the invention are administrated with implanted mini-pumps and/or devices and/or dosages forms suitable for long period deliveries in the body.

DETAILED DESCRIPTION OF THE INVENTION AND PREFERRED EMBODIMENTS

Compositions

In one embodiment, the present invention provides a pharmaceutical composition comprising: (i) a compound of Formula I; and (ii) an antidiabetic agent. Advantageously, the compositions of the present invention provide clinical advantage over the use of a single agent alone.

Based on the unique features of the compounds of Formula I, the combination of one of these compounds with one or more antidiabetic agents described herein provides a significant clinical advantage over the use of a single agent alone. Thus, (1) the combination of a compound of Formula I (which is thought to increase peripheral tissue sensitivity to insulin) with either insulin therapy, or a stimulator of insulin secretion (e.g., a sulfonylurea) increases the efficacy of either agent alone, and moreover, allows for the reduction in dosage of all agents used in the combination therapy. In addition, (2) the combination therapy between a compound of Formula I and one or more other agents that increase insulin sensitivity (e.g., biguanides, glitazones, RXR ligands, PPAR.gamma. agonists, and the like.), results in an enhanced effect between the various agents, with reduction in the side effects normally associated with these other agents. Further, (3) compounds of Formula I can be administered in combination with antidiabetic agents whose mode of action is other than stimulation of insulin secretion or insulin sensitivity (e.g., .alpha.-glucosidase inhibitors, potassium channel antagonists, aldose reductase inhibitors, glucagon antagonists, RXR ligands and anti-obesity agents). Importantly, these types of combinations result in enhanced efficacy relative to the use of a single agent alone. In addition, the present invention includes (4) a combination treatment comprising a compound of Formula I in combination with agents aimed at treating any one of the conditions often associated with diabetes, such as obesity, cardiovascular diseases, cerebrovascular diseases, thrombosis, ischemia, hypoxia, hypertension, hypercholesterolemia and other lipid disorders, peripheral neuropathies and other neurological disorders. Furthermore, (5) the combination therapy between a compound of Formula I and one or more other agents that increase insulin sensitivity (e.g., biguanides, glitazones, RXR ligands, PPAR.gamma. agonists, and the like.), results in a prevention of diabetic troubles or conditions or in a delaying of the appearance of diabetic troubles or conditions.

The compounds of Formula I, particularly glycine betaine, are known to possess antiaggregant, anticoagulant, anti-adhesives, anti-inflammatory and fibrinolytic properties. The exact potency and intrinsic agonist activity of each compound of Formula I is a function of the compound's structure in a relatively predictable manner.

In an embodiment of the invention the compounds of Formula I, preferably glycine betaine (n=1) can be used for therapeutic and/or dietary supplementation as to manage diabetes.

According to the invention, therapeutic and/or dietary betaines supplementation may represent a potentially useful strategy for the management of diabetes. Betaine is a stable amino acid in an aqueous solution, and is not destroyed by sterilization conditions (e.g., high temperature and high pressure). In addition, betaine is nontoxic, and its administration is generally safe for both humans and animals. Betaine can be useful in the treatment of patients with type I diabetes, when been used along with insulin therapy to increase insulin secretion by the remaining pancreatic β-cells and improve insulin sensitivity in tissues via enhanced production of NO. This can help reduce the dosage and frequency of insulin therapy for patients with type I diabetes, while improving protein balance and endothelial function. In patients with type II diabetes, the pancreas is exhausted from the overproduction of insulin to overcome the insulin resistance of tissues, and most clinicians do not use drugs or agents that stimulate insulin secretion to treat this type of diabetes.

In one embodiment, betaine treatment can increase the plasma concentration of insulin in patients with type II diabetes. However, betaine supplementation may be a promising method of improving cardiovascular function in patients with type II diabetes by increasing endothelial NO synthesis. In support of this view, recent studies indicate that intravenous infusion of betaine (30 g over 30 min) reduces blood pressure and improves haemodynamic functions in patients with type II diabetes. Thus, dietary betaine supplementation may enhance insulin sensitivity and attenuate or even prevent insulin resistance, thereby eliminating the need for the additional insulin therapy that is often required with sulfonylurea.

In one embodiment, therapeutic and/or dietary betaine supplementation reduces body weight loss (in diabetic patients), improves glucose homeostasis, increases plasma and endothelial concentrations of betaine, enhances endothelial $BH_4$ availability for NO synthesis, enhances endothelial NO synthesis, improves circulation and lessens hypertension in the diabetic subjects. These findings provide a biochemical basis for the beneficial effect of therapeutic and/or dietary betaine supplementation in preventing endothelial dysfunction in diabetic subjects.

In one embodiment, one or more compounds of Formula I can be partly or completely in slow, delayed, extended, sustained or controlled release dosage forms when associated to one or more of the anti-diabetics compounds.

In one embodiment, one or more of the anti-diabetics compounds can be partly or completely in slow, delayed, extended, sustained or controlled release dosage forms when associated to one or more compounds of Formula I.

In one embodiment, one or more compounds of Formula I can be partly or completely in slow, delayed, extended, sustained or controlled release dosage forms and are associated to one or more anti-diabetics compounds which are partly or completely in slow, delayed or controlled release dosage forms.

According to the invention, dietary betaine supplementation may represent a potentially useful strategy for the management of juvenile diabetes. To achieve this purpose, betaine and compounds of Formula I can be enclosed in useful dietary products such as chocolate bars, cookies, drinks, meals, sweets, confectioneries and edible products which are usually ingested by young people. According to the invention, dietary and/or edible sweet products can contain one or more of cacao, cocoa, honey, cereals, muesli, nougat, caramel, seeds, kola, mint, fruits, fruit aromas, sugar, molasses and an efficient amount of one or more compound of Formula I. Such products might be particularly useful in the management of diabetes while allowing higher carbohydrates daily intake. In one particular embodiment, due to the cardiovascular properties of the compounds of Formula I, such dietary and/or edible sweet products can also be used in the management of cardiovascular risks in persons in need, i.e. at risk to develop cardiovascular events.

Diabetic chocolates are usually sweetened with a type of sugar as 'polyol'. Polyols are used as other sugar alternatives. In summary, polyols such as sorbitol and maltitol are still carbohydrates and the body will turn them, at least in part, into glucose. Polyols can also behave like a laxative, making feel gassy, bloated and giving you stomach ache. Betaine supplementation avoids these kinds of side effects.

In one embodiment, a chocolate composition containing cocoa and compounds of formula I are claimed. Glycine betaine due to its sweet taste can be preferred. The betaine can be mixed with the chocolate paste at the end of the manufacturing process of the chocolate. A chocolate bar containing betaine for diabetics is claimed. Disclosed and claimed are cocoa extracts, compounds, combinations thereof and compositions containing the same and further containing one or more compound of Formula I, glycine betaine being preferred for its sweet taste. In one embodiment the chocolate bar will be sensibly free of sugar and carbohydrates, betaine fulfilling their sweetening effects while having its cardiovascular and antidiabetic effects.

In one embodiment, the chocolate composition can be, chocolate pasta such as spread pasta.

In one embodiment the chocolate composition containing cacao and one or more compound of formula I is sweetened by polyols such as sorbitol, tagatose and maltitol. Tagatose is derived from lactose can constitute an interesting alternative according to the present invention.

Although older studies found that, similarly to fructose, sugar alcohols (i.e., sorbitol, xylitol, maltitol, mannitol) induced low glycemic responses, more recent studies have found that some sugar alcohols, notably maltitol, induce no less of a glucose surge than glucose itself when used in certain products, such as chocolate. Maltitol is used frequently in "sugar-free" chocolate and other candies, so this effect is clinically meaningful. Other sugar alcohols, such as sorbitol, lactitol, and xylitol appear to raise blood glucose and insulin levels substantially less than glucose and for this reason are being used with increasing frequency as sweeteners in the creation of "sugar-free" products. They are incompletely absorbed in the digestive tract, and as a result, have a lower calorie content than sugar (range, 1.5 to 3 kcal/g). Diet products, especially those aimed at low-carbohydrate dieters, seek to position themselves as lower calorie and lower carbohydrate, and thus, better for weight loss. Because sugar alcohols and fiber are not completely metabolized, there is a trend toward subtracting them from the carbohydrate count reported on the nutrient facts panel. This results in the "net" carbohydrate count, which is substantially lower than the actual carbohydrate content. This is primarily a food marketing scheme to promote products as "dietetic" or "healthy" and "low carb." It is another goal of the present invention to provide chocolate formulations where one or more compounds of Formula I, preferably glycine betaine, is admixed with cocoa and one or more sugar such as glucose, sacharrose, sorbitol, lactitol, tagatose, xylitol, fructose, sugar alcohols, maltitol, mannitol and the sugars known, by the skilled person, to serve to chocolate manufacture. Compounds of formula I supplementation in all known chocolate formulations will be suitable to obtain a "diabetic chocolate". Due to the numerous pharmacological properties previously described by the inventor, such chocolate with betaine can also claim "cardiovascular chocolate", "dietetic", "healthy" and "low carb." chocolate. The amounts of betaine per weight of chocolate can be adjusted depending of the type of dietetic claim, the type of pharmacological claim and/or the type of patient.

In one embodiment the chocolate composition can be sensibly free of sugars.

In one embodiment betaine and compounds of Formula I can be enclosed in useful dietary products such as chocolate bars, cookies, drinks, meals, sweets, confectioneries and edible products destined specifically to persons suffering or at risk to suffer of diabetes mellitus, hyperlipemia and impaired glucose tolerance.

Examples of Products:

Milk Bar Ingredients: Maltitol, Cocoa Butter, Milk Powder, Cocoa Mass, Butter Oil, Soya Lecithin, Natural Vanilla and sufficient amount of betaine Dark Bar Ingredients: Maltitol, Cocoa Mass, Cocoa Butter, Soya Lecithin, Natural Vanilla and sufficient amount of betaine White Bar Ingredients: Maltitol, Cocoa Butter, Milk Powder, Butter Oil, Soya Lecithin, Natural Vanilla and sufficient amount of betaine Compounds of Formula I have been shown, in diabetic patients to normalize fastening blood glucose levels with the anti-diabetic efficacy of the glitazones, but with a decreased propensity to induce body weight gain. One of the major side effects of glitazones (e.g., troglitazone, rosiglitazone and pioglitazone) is their obesity-inducing potential. Advantageously, compounds of Formula I possess a diminished propensity towards inducing body weight gain and thus, avoiding one of the major side effects of known glitazones. In one embodiment, the use of the compounds of Formula I are claimed to normalize body weight in a mammal in need. Moreover, compounds of Formula I have also shown beneficial effects on plasma lipid profiles.

Moreover, in certain embodiments, additional compounds can be mixed with the compounds of Formula I and are described in WO 99/38845, published Aug. 5, 1999, to De La Brouse-Elwood et al., and incorporated herein by reference in its entirety for all purposes. Certain compounds as described therein, are potent, selective activators of PPAR.gamma and are useful for the treatment of NIDDM and other disorders related to lipid metabolism and energy homeostasis. In other aspects, and depending on the biological environment (e.g., cell type, pathological condition of the host, and the like.), the compounds can activate or block the actions of PPAR-.gamma. By activating the PPAR.gamma receptor, the compounds will find use as therapeutic agents capable of modulating conditions mediated by the PPAR.gamma receptor. Additionally, the compounds are useful for the prevention and treatment of complications of diabetes (e.g., neuropathy, retinopathy, glomerulosclerosis, and cardiovascular disorders), and treating hyperlipidemia. The compounds are useful for the modulation of inflammatory conditions which most recently have been found to be controlled by PPAR.gamma. (see, Ricote, et al., Nature, 391:79-82 (1998) and Jiang, et al., Nature, 391:82-86 (1998). Examples of inflammatory conditions include rheumatoid arthritis and atherosclerosis Compounds that act via antagonism of PPAR.gamma are useful for treating obesity, hypertension, hyperlipidemia, hypercholesterolemia, hyperlipoproteinemia, and metabolic disorders.

Preferred compound of Formula I are those in which n=1 is i.e. glycine betaine. But at least one or more of the betaines of Formula I can be used according to the invention alone to achieve the therapeutical purposes of the invention. One or more of the betaines of Formula I, can also be used in mixtures or in combinations with the antidiabetic compounds of the invention to achieve the therapeutical purposes of the invention.

The compositions of the present invention further comprises one or more (ii) antidiabetic compounds. A wide range of antidiabetic agents can be used in the compositions and methods of the present invention. Suitable agents include, but are not limited to, one or more antidiabetic agent such as sulfonylureas, biguanides, glitazones and other PPAR-.gamma. agonists, alpha.-glucosidase inhibitors, potassium channel antagonists, aldose reductase inhibitors, glucagon antagonists, activators of RXR, insulin therapy or other anti-obesity agent, prodrugs thereof, or pharmaceutically acceptable salts of the antidiabetic agents. In certain instances, the antidiabetic agents include, but are not limited to, one or more agents such as insulin and insulin analogs (e.g. LysPro insulin); GLP-1 (7-37) (insulinotropin) and GLP-1 (7-36)-NH-.sub.2; sulfonylureas and analogs, including, but not limited to, chlorpropamide, glibenciamide, tolbutamide, tolazamide, acetohexamide, glipizide, glimepiride, repaglinide and meglitinide; biguanides, including, but not limited to, metformin, phenformin and buformin. The methods of treatment combining the uses of one or more of the antidiabetic agents, as described in the present application, with the compounds of Formula I for treating the pathologies, as described in the present application, are also claimed.

In one embodiment, the combined compounds of the invention are claimed to treat, alleviate and/or provide method of treatment to diabetic associated conditions such as: diabetic retinopathy, heart disease, mouth conditions, proteinuria, retinal detachment, transient ischemic attack, hypertension, pulmonary hypertension, portal hypertension, obesity, high cholesterol, diabetic retinopathy, heart disease, etc.

In one embodiment, the compounds of Formula I can be associated to endothelin antagonist such as bosentan to treat endothelin related pathologies, among them pulmonary hypertension.

In one embodiment, the associations of the present application, namely one or more of the compounds of Formula I, and one or more antidiabetic agents, can be further associated and/or combined with one or more therapeutic agent selected from the group consisting in: aspirin, polyphénols, vitamins, dhea, statins, bi-aspirin, antioxidants, etc.

In one embodiment, the compounds of Formula I, when used alone are claimed to treat, alleviate and/or provide method of treatment to diabetic associated conditions such as: diabetic retinopathy, heart disease, mouth conditions, proteinuria, retinal detachment, transient ischemic attack, hypertension, pulmonary hypertension, portal hypertension, obesity, high cholesterol, diabetic retinopathy, heart disease, etc.

In another embodiment, the antidiabetic agents include various forms of insulin, such as insulin in its various dosage forms, subcutaneous, oral, inhaled, and the like, molecular variations, and short-, medium- and long-acting versions. Suitable insulin sources include, but are not limited to, recombinant human insulin, natural pig insulin, natural ox insulin, natural bovine insulin, natural human insulin, recombinant human argine-insulin, recombinant human aspartic-insulin, dalanated insulin, defalan insulin, glargine insulin, human insulin zinc, human insulin isophane, lispro insulin, neutral insulin, human proinsulin, their mixtures and the like.

In one embodiment, the antidiabetic agents used in the compositions of the present invention are sulfonylureas. Preferred sulfonylureas suitable for use in the present invention include, but are not limited to, acetohexamide, chlorpropamide, glyburide, glipizide, gliclazide, glimepiride, gliquidone, glisoxepid, glibomuride, gliamilide, glibomuride, glicetanile, gliflumide, glymidine, glyparamide, tolpyrramide, glyhexamide, phenbutamide, tolazamide, tolbutamide, tolcyclamide and their mixtures. Those of skill in the art will know of other sulfonylureas suitable for use in the present invention.

Sulfonylureas are a group of drugs that induce hypoglycemia by stimulating insulin release from the pancreas. Generally, sulfonylureas have found wide utility in the treatment of NIDDM. Their efficacy is decreased in IDDM because of the inherent inability of the patient to produce insulin. Adverse reactions to sulfonylureas occur in a fraction of patients, particularly the elderly. One of the most severe side effects is hypoglycemia and coma. Other side effects include nausea and vomiting, cholestatic jaundice, agranulocytosis, cardiovascular mortality, aplastic and hemolytic anemias, generalized hypersensitivity reactions and dermatological reactions. The compounds of Formula I increase insulin sensitivity, and when used in combination with sulfonylureas, increase the efficacy and side effect profile of either type of agent alone. In certain instances, the combination therapy allows the use of lower doses of both agents.

In a preferred embodiment, the antidiabetic agents used in the compositions of the present invention are biguanides. Biguanides are a group of drugs that are efficacious in the treatment of hyperglycemia. Preferred biguanides suitable for use in the present invention include, but are not limited to, metformin, phenformin and buformin. Unlike the sulfonylureas, metformin does not induce release of insulin from the pancreas. Without being bound by any particular theory, it is thought that its effects are mediated by increasing insulin activity in peripheral tissues, reducing hepatic glucose output due to inhibition of gluconeogenesis and reducing the absorption of glucose from the intestine. Side effects associated with the use of biguanides include lactic acidosis, diarrhea, nausea, and anorexia. Preferred biguanides include metformin, buformin, etoformin and phenformin.

In another embodiment, the antidiabetic agent is a glitazone. Glitazones, also known as thiazolidinediones, ciglitazone, darglitazone, englitazone, AD-5075, and BM-131246. Preferably, the glitazone compounds used in the present invention include troglitazone, rosiglitazone, and pioglitazone.

As disclosed therein, oxyiminoalkanoic acid derivatives are disclosed that are useful for treating and/or preventing diabetes mellitus, hyperlipemia, impaired glucose tolerance, inflammatory disease and arteriosclerosis. Moreover, the compounds are useful for controlling retinoid-related receptors, enhancing insulin sensitivity and improving insulin resistance, and for treating and preventing diabetic complications. Other PPAR.gamma. modulators are disclosed in WO 99/38850, published Aug. 5, 1999, to Lohray et al., and incorporated herein by reference in its entirety for all purposes.

In another embodiment, the present invention provides compositions comprising compounds of Formula I and alpha.-glucosidase inhibitors. Preferred .alpha.-glucosidase inhibitors include acarbose, celgosivir, camiglibase, voglibose and miglitol. Suitable .alpha.-glucosidase inhibitors are disclosed in WO 99/29327, to Odaka et al., published Jun. 17, 1999, entitled "Use of an a-glucosidase inhibitor to treat high-risk impaired glucose tolerance" and incorporated herein by reference in its entirety for all purposes. As described therein, the .alpha.-glucosidase inhibitor is particularly useful in the treatment of non-insulin-dependent diabetes mellitus. In addition, WO 99/26606, published Jun. 3, 1999, to Goldman et al., and entitled "Sustained-release formulations of .alpha.-glucosidase inhibitors," and incorporated herein by reference in its entirety for all purposes, discloses sustained released formulations of .alpha.-glucosidase inhibitors, (e.g. acarbose useful in the present invention).

Other types of agents that have found limited utility in treating diabetes include potassium channel antagonists such as repaglinide, and aldose reductase inhibitors such as zopolrestat, minalrestat, ponalrestat and tolrestat. Still in the experimental stage, glucagon antagonists, activators of the retinoid-X receptor (RXR), and anti-obesity agents are also being evaluated as potential antidiabetic agents. Others agents suitable for use in the present invention include, but are not limited to, glucagon, and miscellaneous agents such as methyl palmoxirate, palmoxirate sodium, pirogliride, pramlintide, amlintide, seglifide.

Methods, Uses, Dosages and Schedules

In another embodiment, the present invention provides a method for modulating conditions associated with diabetes or diabetes-related disorders in a host, comprising administering to the host an efficacious amount of compositions comprising (i) a compound of Formula I in combination with (ii) one or more antidiabetic agents. In certain aspects, the compositions of the present invention that are administered comprise a compound of Formula I formulated together with one or more antidiabetic agents. Alternatively, the composition that is administered comprises a compound of Formula I independently formulated from one or more antidiabetic agents i.e., separately formulated.

The pharmaceutical compositions of the present invention are suitable for use in a variety of drug delivery systems. Examples of suitable formulations for use in the present invention are found in Remington's Pharmaceutical Sciences (Mack Publishing Company, Philadelphia, Pa., 17th ed. (1985)), which is incorporated herein by reference. In addition, for a brief review of methods for drug delivery, see, Langer, Science 249:1527-1533 (1990), which is incorporated herein by reference. The pharmaceutical compositions of the present invention are intended for parenteral, topical, oral or local administration. In certain aspects, the pharmaceutical compositions are administered parenterally, (e.g., intravenously, subcutaneously, intradermally, or intramuscularly). In one embodiment, the invention provides compositions for parenteral administration which comprise a compound of Formula I, an antidiabetic agent as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well-known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid formulations, compounds of Formula I can be admixed with conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the compounds of Formula I and antidiabetic agents are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, (e.g., lecithin for intranasal delivery).

The compounds of the present invention can be prepared and administered in a wide variety of oral, enteral and parenteral dosage forms. Thus, the compounds of the present invention can be administered by injection, that is, intravenously, intramuscularly, intracutaneously, subcutaneously, intraduodenally or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of Formula I or a pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is a finely divided solid that is in a mixture with the finely divided active component. In tablets, the active component is mixed with the carrier having the necessary binding properties in suitable proportions and compacted in the shape and size desired.

The powders and tablets preferably contain from 5% to 95% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as blisters, packeted tablets, capsules, and powders and/or beads in vials, bags, sachets or ampoules. Also, the unit dosage form can be a capsule, tablet, cachet, or lozenge itself, or it can be the appropriate number of any of these in packaged form.

The quantity of active components in a unit dose preparation may be varied or adjusted from 0.1 mg to 10000 mg, preferably 1.0 mg to 5000 mg according to the particular application and the potency of the active component. The composition can, if desired, also contain other compatible therapeutic agents.

In therapeutic use especially for the treatment of obesity, NIDDM, or inflammatory conditions, the antidiabetic compounds utilized in the pharmaceutical method of the invention are administered at the initial dosage of about 0.001 mg/kg to about 500 mg/kg daily. A daily dose range of about 0.1 mg/kg to about 150 mg/kg is preferred. Most preferably, the daily dose range is comprised between 1 mg/kg and 100 mg/kg, especially between 2 mg/kg and 25 mg/kg. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages that are less than the optimum dose of the compound. Thereafter, the dosage is increased by small increments until the optimum effect under circumstances is reached. For convenience, the total daily dosage may be divided and administered in portions during the day, if desired.

In therapeutic applications, the compounds of Formula I and antidiabetic agents of the present invention are administered to a patient in a combination amount sufficient to elicit a response. An amount adequate to accomplish this is defined as "therapeutically effective combination dose." The methods include the administration of the combination of compound of Formula I with antidiabetic agent wherein the two components are delivered in a simultaneous manner, in combination therapy wherein the compound of Formula I is administered first, followed by the antidiabetic agent, as well as wherein the antidiabetic agent is delivered first followed by the compound of Formula I.

The betaine of Formula I utilized in the pharmaceutical method of the invention is administered at the initial dosage of about 0.001 mg/kg to about 500 mg/kg daily. A daily dose range of about 0.1 mg/kg to about 150 mg/kg is preferred. Most preferably, the daily dose range is comprised between 1 mg/kg and 100 mg/kg, especially between 25 mg/kg and 75 mg/kg.

Since the present invention has an aspect that relates to a combination of active ingredients which can be administered separately, the invention also relates to combining separate pharmaceutical compositions in kit form. The kit comprises two separate pharmaceutical compositions: a compound of Formula I, a prodrug thereof or a pharmaceutically acceptable salt and a second compound such as an antidiabetic agent as described above. The kit comprises a container for containing the separate components such as a divided bottle or a divided foil packet, however, the separate components can also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Effective combination amounts for various uses will depend on, for example, the particular antidiabetic agent, the compound of Formula I employed, the manner of administration, the weight and general state of health of the patient, and the judgment of the prescribing physician. In one embodiment, composition or formulation to be administered will contain a quantity of a compound(s) according to Formula I in an amount effective to treat the disease/condition of the subject being treated, (e.g., a glycogen phosphorylase dependent disease/condition). The amount of antidiabetic agent will depend in part to the chemical class.

In certain instances, administration of the compounds of Formula I can be via any method which provides systemic exposure to the compound of this invention, preferably to the muscle and fatty tissue. These methods include oral routes, enteral, parenteral, intraduodenal routes, etc. Generally, the compounds of the present invention are administered in single (e.g., once daily) or multiple doses. The compounds of the present invention are generally administered in the form of a pharmaceutical composition comprising at least one of the compounds of Formula I together with a pharmaceutically acceptable carrier or diluent. Thus, the compounds of this invention can be administered individually or together in any conventional oral, parenteral or transdermal dosage form.

For oral administration, a pharmaceutical composition can take the form of solutions, suspensions, tablets, pills, capsules, powders, and the like. Tablets containing various excipients such as sodium citrate, calcium carbonate and calcium phosphate are employed along with various binders such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules, preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

In one embodiment, the combined compounds in the form of a powder, granules, microgranules, microspheres, pellets and gels. The combined compounds can be in the form of a pharmaceutical unit dosage form said dosage form being selected from the group consisting of sachets, pouches, blisters and bags Pharmaceutical unit dosage form of a composition containing at least a betaine, said dosage form being selected from the group consisting of sachets, pouches, blisters and bags, wherein the pharmaceutical unit dosage form is provided with moisture barrier property defined by an increase of weight of the composition of less than 1% after storage of the unit dosage form in sealed condition in an environment with a temperature of 38° C. and a relative humidity of 90% during 30 days.

Such individual sachet being possibly further submitted to an encrypting against counterfeiting and/or a notch to facilitate the tearing and/or the opening.

As MVTR stands for "Moisture Vapor Transmission Rate", a measure of the passage of gaseous $H_2O$ through a barrier, the pharmaceutical oral unitary dose of betaine in a sealed dosage form from the group consisting of sachets, bags, blisters and pouches in which the dosage form is at least partly flexible, water impermeable and characterized by a protective barrier by a MVTR value inferior to 0.1 $g/m^2$ at 38° C. and 90% relative humidity during 24 hours.

In one embodiment, the sizes of the betaines particles can be selected so as to absorb minimally the water (for instance from micronized particles to an optimal size particles allowing a minimal water intake). Optionally the particles (or the dosage form such as a sugar-coated pill could be further enveloped by a surfactant having good moisture barrier) can be sugar-coated and optionally such particles can be trapped in a gel or a polymer before being packaged in a selected MVTR container or pharmaceutical unit dosage form.

For example the coating or primary packaging material could be a laminate which is made up of 12 µm PET, 25 µm Alufoil and a 50 µm PE inner heat-seal layer. Further high quality and clarity of surface decoration might be realized by gravure reverse printing process.

The complete barrier requirement for this highly hygroscopic product (betaine after being dried, i.e. its liquid content partially or completely removed) could be provided by a laminate of PET, PE and Alufoil. The single 250 to 5000 mg doses are easy to tear open and safe for mouth contact In this dosage form betaine can be taken directly by mouth without the need to dissolve in water. Some flavoring agents might be added to mask betaines taste by the way augmenting patients' compliance. Geometrical forms which augment the facility of use can be privileged.

In one embodiment a stick format of the sachet will be preferred as it uses a minimum amount of material in relation to the volume of its contents and further by reducing the bag surface it allows also to reduce the MVTR.

The dosage forms can be optimized according to selected combinations of MVTR, betaine doses, tensile strengths, sizes, forms, coefficients of friction. The initial rate of moisture of the betaines can also be selected and/or controlled so as to lower the other parameters (MVTR, etc) thus augmenting the compliance of the dosage form.

Betaine monohydrate and/or Betaine anhydrous and/or theirs mixtures solutions after being submitted to the processes of the invention can be dried and sachets as unit oral dosage forms of betaine(s) can be realized using as primary packaging material multilayer Alufoil material. The realized sachets will be weighted just after their manufacture and 1, 3, 6 and 12 months later, so as to determine the possible water intake of the betaine(s) inside the sealed dosage forms. The results could show that the weight variation is in accordance and in the limits allowed by the International Pharmacopoeia and come up to the FDA and/or BGA directives and the recommended and approved instructions given by EF for this kind (sachets/blister/pouches) of pharmaceutical dosage form. Due to the high hygroscopic properties of betaines, in one embodiment betaine monohydrate can be preferred. In effect the water intake of betaine monohydrate can be in a preliminary step controlled so as to avoid/control further moisture intake.

In one embodiment Betaine monohydrate and/or Betaine anhydrous and/or theirs mixtures are used "as is", i.e. as provided in pharmaceutical grade (suitable for oral use) by the manufacturers after the sugar beet molasses separation processes or the chemical or biological synthesis. These betaines can be packaged in such unit oral dosage form sachets having such moisture and/or oxygen and/or light barriers and/or tensile strength and/or coefficient of friction.

The coefficients of friction outside/outside and/or inside/inside will have to be carefully chosen so as to allow the maximum of the compound to be delivered at the administration. When absorbing moisture the betaine can start a process of higher size crystallization which can adhere inside the sachet making a part of the betaine unavailable upon administration. In the other side such medicament being destined to a daily utilisation during years, it is necessary to carefully choice the physical properties of the primary packaging material so as to have at the same time a good moisture barrier while having an easy opening, i.e. a "friendly" tensile strength allowing for instance elderly people to take easily their daily or twice daily medication. The primary packaging material must be easy to tear while possessing good moisture and/or oxygen barriers, such barriers preventing betaines deliquescence. Moisture sorption could lead to betaine particles agglomeration which can then adhere inside the sachet leading to a partial delivery of the drug after tearing. When carefully choose, selected and combined these parameters will allow compliance with the International Pharmacopoeia and Pharmaceutical Industry standards as they (parameters) will allow a better compliance of the end user, i.e. the patient. All the combinations do not work and only a careful selection of specific materials with particular parameters can provide this double compliance of sachet oral unit dosage forms of betaines.

Thus it is claimed here the combinations of the above physical characteristics of betaines forms (salts, sizes, coatings, polymers, etc) and the physical characteristics of the packaging materials (MVTR, tensile strength, coefficient of friction, tear strength, etc) which (the combinations) allow to augment the compliance of the pharmaceutical dosage form while retaining and respecting correct (according to international regulations and directives) conservation properties.

In one embodiment, the compounds of Formula I and/or the antidiabetic compounds and/or the combined compounds of the invention can be manufactured in formulations, forms and dosages forms such as those claimed in WO0051596, US 20020065320, WO02062322, US 20040033223, WO2004049095, WO2004091601, BE 2004/0364, PCT/BE 2004/00110, PCT/BE 2004/000163 of the inventor.

According to the invention it will be appreciated that the actual preferred course of therapy will vary according to, inter alia, the mode of administration of the compound of Formula I, the particular formulation of the antidiabetic agent being utilized, the mode of administration of the compounds, the particular disease being treated and the particular host being treated. The optimal course of therapy for a given set of conditions can be ascertained by those skilled in the art using conventional course of therapy determination tests and in view of the information set out herein.

Additional Uses for Compounds of Formula I

The compounds of Formula I have been recently shown to enhance nitric oxide production in human and other species. As such, specific compounds of Formula I are well suited for the treatment of the various conditions and diseases established to be mediated by, or linked to nitric oxide levels. Thus the compounds of Formula I can be suitable to treat below outline other indications alone or in combinations with the antidiabetic compounds of the present invention.

Metabolic Conditions such as: Diabetes and Conditions Secondary to Diabetes, Hypertension, Angina pectoris, Dyslipidemia, Hypertriglyceridemia, Gout, Hyperlipoproteinemias, Hypercholesterolemia, Nephropathy and other renal diseases secondary to diabetes, Diabetic neuropathy, other insulin-resistance-related diseases, polycystic ovarian syndrome, glucocorticoid-induced insulin resistance.

Obesity, promote adipocyte differentiation and fat.

Hypertension, suppress or lower or cross endothelin-1 secretion by vascular endothelial cells and result in decreased blood pressure.

Lipid Disorders, been implicated in systemic glucose and lipid homeostasis.

Bone Disorders.

Female specific conditions where Formula I compounds can be used to inhibit excessive uterine bleeding in women and also to alleviate hormones disorders in menopausal women Male hormone disorders such as andropause related disorders.

Acne and other skin disorders associated with differentiation of epidermal cells as proliferative diseases of the skin.

CNS, Alzheimer's, Neuroinflammation, such as ischemic stroke, closed-head injury, and multiple sclerosis.

Chemotherapy, Cancer.

Inflammation/Immune disorders.

Ophthalmic, Macular Degeneration

3. Antiangiogenic

The invention will be described in greater detail by way of specific examples. The following examples are offered for illustrative purposes, and are not intended to limit the invention in any manner.

EXAMPLES

Example 1

Dosage form with metformin and betaine anhydrous: Sachet comprising unit powder dosage form of 500 mg metformin and 2000 mg glycine betaine The dosage form of example 1 has been repeated excepted that metformin and glycine betaine are mixed together with a granulating agent, extruded and spheronized in beads of about 1 mm, The beads have been coated with eudragit, said eudragit being mixed in an organic solvent and sprayed on the beads, where after the beads are dried.

Example 2

This example illustrates combination therapy of a compound of Formula I and a metformin by oral administration.

Patients having NIDDM (Type II diabetes mellitus) are selected for therapy. The patients weigh between 70-100 kilograms. A compound of Formula I is orally administered in a dosage of 1 to 15 grams twice daily, more typically 100 mg/kg twice daily. For infants or children the doses suggested are lowered in a linear fashion based on body weight or surface area.

Half the patient population is administered metformin as well as a compound of Formula I using an effective dose of both agents. The other half of the patients are administered an effective dose of metformin. The patients are monitored for improvement in the manifestations of the disease and for side effects, such as body weight gain and signs of liver toxicity.

The combined compounds of the invention increased the patients' body's sensitivity to insulin and lowered glucose fasting levels.

The results indicate the administration of a combination of i) a compound of Formula I with ii) metformin increases the efficacy of either agent alone. The composition also provides concomitant decrease in the side effects of either agent alone.

Example 3

Capsule containing glyburide and betaine anhydrous: Sachet comprising unit powder dosage form of 1 mg glyburide and 1000 mg glycine betaine All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A pharmaceutical combination for treating diabetes mellitus, said combination comprising a therapeutically effective amount of metformin and a therapeutically effective amount of a pharmaceutically acceptable betaine selected from the group consisting of glycine betaine anhydrous, glycine betaine monohydrate and mixtures thereof.

2. The pharmaceutical combination of claim 1, in which the weight ratio therapeutically effective amount of metformin/therapeutically effective amount of pharmaceutically acceptable betaine is comprised between 1:10 and 10:1.

3. The pharmaceutical combination of claim 1, in which the weight ratio therapeutically effective amount of metformin/therapeutically effective amount of pharmaceutically acceptable betaine is comprised between 1:8 and 8:1.

4. The pharmaceutical combination of claim 1, in which the weight ratio therapeutically effective amount of metformin/therapeutically effective amount of pharmaceutically acceptable betaine is comprised between 1:5 and 5:1.

5. The pharmaceutical combination of claim 1, in which the weight ratio therapeutically effective amount of metformin/therapeutically effective amount of pharmaceutically acceptable betaine is greater than 1.

6. The pharmaceutical combination of claim 1, which comprises an oral controlled release form comprising the metformin.

7. The pharmaceutical combination of claim 6, in which the oral controlled release form comprises less than 3 g of metformin.

8. The pharmaceutical combination of claim 1, which comprises an oral controlled release form comprising less than 2.5 g of the metformin.

9. The pharmaceutical combination of claim 1, which comprises an oral controlled release form comprising less than 2 g of the metformin.

10. The pharmaceutical combination of claim 1, which comprises an oral controlled release form comprising a therapeutically effective amount of less than 2.5 g of the metformin.

11. The combination of claim 1, which comprises an oral controlled release form comprising pharmaceutically acceptable betaine.

12. The combination of claim 1, which comprises an oral controlled release form comprising the therapeutically effective amount of the pharmaceutically acceptable betaine.

13. The pharmaceutical combination of claim 3, which comprises a therapeutically effective amount of more than 1 g pharmaceutically acceptable betaine.

14. The combination of claim 1, which comprises an oral controlled release form comprising the therapeutically effective amount of more than 1.5 g of the pharmaceutically acceptable betaine.

15. The combination of claim 1, which comprises an oral controlled release form comprising the therapeutically effective amount of more than 2 g of the pharmaceutically acceptable betaine.

16. The pharmaceutical combination of claim 1, which has the form of at least one solid or semi-solid unit for oral administration.

17. The pharmaceutical combination of claim 16, in which the at least one solid or semi solid unit form is selected from the group consisting of beads and particles comprising metformin, whereby said beads and particles are provided with a water insoluble polymer coating, said coating being entero soluble.

18. The pharmaceutical combination of claim 16, in which the said at least one solid or semi-solid unit form is selected from the group consisting of beads and particles comprising pharmaceutically acceptable betaine, said beads and particles being provided with a water insoluble polymer coating, said coating being entero soluble.

19. The pharmaceutical combination of claim 1, which has the form of at least one solid or semi-solid unit for oral administration, whereby the said at least one solid or semi solid unit for oral administration is selected from the group consisting of beads and particles comprising metformin and pharmaceutically acceptable betaine, and beads and particles being provided with a water insoluble polymer coating, said coating being entero soluble.

20. The pharmaceutical combination of claim 1, in which the therapeutically effective amount of the metformin and the therapeutically effective amount of the pharmaceutically acceptable betaine are placed in one single sealed bag.

21. The pharmaceutical combination of claim 20, in which each bag forms a unit dose comprising from 500 mg to 3000 mg metformin and from 500 mg to 6000 mg pharmaceutically acceptable betaine.

22. A method for treating a human suffering from diabetes mellitus, said method comprising the step of administering orally at least daily a pharmaceutical combination comprising a therapeutically effective amount of metformin and a therapeutically effective amount of a pharmaceutically acceptable betaine selected from the group consisting of glycine betaine anhydrous, glycine betaine monohydrate and mixtures thereof.

23. The method of claim 22, in which the weight ratio therapeutically effective amount of metformin/therapeutically effective amount of pharmaceutically acceptable betaine of the administered pharmaceutical combination is comprised between 1:10 and 10:1.

24. The method of claim 22, in which the weight ratio therapeutically effective amount of metformin/therapeutically effective amount of pharmaceutically acceptable betaine of the administered pharmaceutical combination is comprised between 1:8 and 8:1.

25. The method of claim 22, in which the weight ratio therapeutically effective amount of metformin/therapeutically effective amount of pharmaceutically acceptable betaine of the administered pharmaceutical combination is comprised between 1:5 and 5:1.

26. The method of claim 22, in which the weight ratio therapeutically effective amount of metformin/therapeutically effective amount of pharmaceutically acceptable betaine of the administered pharmaceutical combination is greater than 1.

27. The method of claim 22, which comprises the step of administering at least daily an oral controlled release form comprising the metformin.

28. The method of claim 22, which comprises the step of administering at least daily an oral controlled release form comprises less than 3 g of metformin.

29. The method of claim 22, which comprises the step of administering at least daily an oral controlled release form comprising less than 2.5 g of the metformin.

30. The method of claim 22, which comprises the step of administering at least daily an oral controlled release form comprising less than 2 g of the metformin.

31. The method of claim 22, which comprises the step of administering at least daily an oral controlled release form comprising a therapeutically effective amount of less than 2.5 g of the metformin.

32. The method of claim 22, which comprises the step of administering at least daily an oral controlled release form comprising pharmaceutically acceptable betaine.

33. The method of claim 22, which comprises the step of administering at least daily an oral controlled release form comprising the therapeutically effective amount of the pharmaceutically acceptable betaine.

34. The method of claim 22, which comprises the step of administering at least daily an oral controlled release form comprising a therapeutically effective amount of more than 1 g pharmaceutically acceptable betaine.

35. The method of claim 22, which comprises the step of administering at least daily an oral controlled release form comprising the therapeutically effective amount of more than 1.5 g of the pharmaceutically acceptable betaine.

36. The method of claim 22, which comprises the step of administering at least daily an oral controlled release form comprising the therapeutically effective amount of more than 2 g of the pharmaceutically acceptable betaine.

37. The method of claim 22, in which the pharmaceutically acceptable betaine is administered before the therapeutic effective amount of the metformin being administered.

38. The method of claim 22, in which the therapeutic effective amount of the pharmaceutically acceptable betaine and the therapeutic effective amount of the metformin are simultaneously administered.

39. A method for modulating conditions associated with diabetes or diabetes-related disorders in a human, comprising administering orally to the human at least daily a pharmaceutical combination comprising a therapeutically effective amount of a metformin and a therapeutically effective amount of a pharmaceutically acceptable betaine selected from the group consisting of glycine betaine anhydrous, glycine betaine monohydrate and mixtures thereof.

* * * * *